(12) United States Patent
Esseiva et al.

(10) Patent No.: US 11,664,091 B2
(45) Date of Patent: *May 30, 2023

(54) ENCODING DATA FROM GENETIC TRAITS RELEVANT TO ILLNESS DIAGNOSIS AND HERITAGE

(71) Applicant: International Business Machines Corporation, Armonk, NY (US)

(72) Inventors: Effron Esseiva, Bowen Island (CA); Franz Friedrich Liebinger Portela, San Pablo de Heredia (CR); Roxana Monge Nunez, San José (CR); Edgar Adolfo Zamora Duran, Heredia (CR)

(73) Assignee: International Business Machines Corporation, Armonk, NY (US)

( * ) Notice: Subject to any disclaimer, the term of this patent is extended or adjusted under 35 U.S.C. 154(b) by 850 days.

This patent is subject to a terminal disclaimer.

(21) Appl. No.: 16/441,690

(22) Filed: Jun. 14, 2019

(65) Prior Publication Data

US 2019/0295693 A1 Sep. 26, 2019

Related U.S. Application Data

(63) Continuation of application No. 15/264,893, filed on Sep. 14, 2016, now Pat. No. 10,347,364.

(51) Int. Cl.
*G01N 33/48* (2006.01)
*G01N 33/50* (2006.01)
(Continued)

(52) U.S. Cl.
CPC .......... *G16B 40/00* (2019.02); *C12Q 1/6816* (2013.01); *G16B 20/00* (2019.02); *G16B 20/20* (2019.02); *G16B 50/40* (2019.02)

(58) Field of Classification Search
CPC ........ G16B 40/00; G16B 20/00; G16B 20/20; G16B 50/40; C12Q 1/6816
See application file for complete search history.

(56) References Cited

U.S. PATENT DOCUMENTS 7,202,943 B2  4/2007 Chang et al.
10,347,364 B2* 7/2019 Esseiva ............... C12Q 1/6816
(Continued)

FOREIGN PATENT DOCUMENTS

| CN | 1445712 A | 10/2003 |
| EP | 1543152 B1 | 3/2011 |
| WO | WO2004114204 A1 | 12/2004 |

OTHER PUBLICATIONS

Drbohlavova et al. Quantum Dots—Characterization, Preparation, and Usage in Biological Systems. International Journal of Molecular Sciences, vol. 10, pp. 656-673. (Year: 2009).*

(Continued)

*Primary Examiner* — Russell S Negin
(74) *Attorney, Agent, or Firm* — Scully, Scott, Murphy & Presser, P.C.; Scott S. Dobson (57) ABSTRACT

Methods and systems are disclosed for encoding and decoding data from genetic traits. In one embodiment, the invention provides a method of encoding data from genetic traits. The method comprises encoding genetic traits information, including using quantum dot wavelengths to identify distinct genetic traits, and using numbers of the quantum dots to represent probabilities associated with the traits. In an embodiment, the invention provides a genetic characteristics decoding system for decoding genetic information encoded using quantum dots in a carrier. The decoding system comprises a light source for charging the quantum dots in the carrier; a scanner for scanning the carrier to retrieve information from the charged quantum dots; and a processing system for processing the retrieved information to determine (Continued)

quantum dot wavelengths to identify distinct genetic traits, and to determine numbers of the quantum dots to identify probabilities associated with the genetic traits.

13 Claims, 11 Drawing Sheets

(51) Int. Cl.
    *G16B 40/00*     (2019.01)
    *G16B 20/00*     (2019.01)
    *C12Q 1/6816*     (2018.01)
    *G16B 50/40*     (2019.01)
    *G16B 20/20*     (2019.01)

(56) References Cited

U.S. PATENT DOCUMENTS

| | | |
|---|---|---|
| 2002/0031783 A1 | 3/2002 | Empedocles et al. |
| 2007/0065074 A1 | 3/2007 | Hillendahl et al. |
| 2008/0159657 A1 | 7/2008 | Kanevsky et al. |
| 2010/0214567 A1 | 8/2010 | Shtatnov |
| 2010/0261153 A1 | 10/2010 | Scholl et al. |
| 2013/0209447 A1* | 8/2013 | Ma ............... A61P 9/10 424/130.1 |
| 2018/0075187 A1 | 3/2018 | Esseiva et al. |

OTHER PUBLICATIONS

Chan e al., "Luminescent quantum dots for multiplexed biological detection and imaging", Current Opinion in Biotechnology 13(1):40-6 • Mar. 2002, pp. 40-46.

Han et al., "Quantum-dot-tagged microbeads for multiplexed optical coding og biomolecules", Nature Biotechnology, vol. 19, Jul. 2001, pp. 631-635.

Craig et al., "Ordering of cosmid clones covering the Herpes simplex virus type I (HSV-I) genome: a test case for fingerprinting by hybridisation", Nucleic Acids Research, vol. 18, No. 9, revised and accepted Mar. 27, 1990, pp. 2653-2660.

Wu et al., "Immunofluorescent labeling of cancer marker Her2 and other cellular targets with semiconductor quantum dots", Nature Biotechnology, vol. 21, Jan. 2003, pp. 41-46.

Chon et al., "Use of Quantum Dot Nanocrystals for Spectrally Encoded Optical Data Storage", Published in: Lasers and Electro-Optics, 2003, CLEO/Pacific Rim 2003; The 5th Pacific Rim Conference on (vol. 1), Dec. 15-19, 2003, p. 379.

Goss et al., "Data Capacity Analysis of Spectrally Encoded", Published in: Information Photonics (IP), 2011 ICO International Conference on; May 18-20, 2011, 2 pages.

Chang et al., "Information coding and retrieving using fluorescent semiconductor nanocrystals for object identification", revised Dec. 19, 2003; accepted Dec. 24, 2003; Jan. 12, 2004, vol. 12, No. 1, Optics Express, pp. 143-148.

Goss et al., "Data detection algorithms for multiplexed quantum dot encoding", revised Feb. 2012, accepted Feb. 16, 2012, published Feb. 24, 2012, Feb. 27, 2012, vol. 20., No. 5, Optics Express, pp. 5762-5774.

List of IBM Patents or Patent Applications Treated as Related.

* cited by examiner

QUANTUM DOTS ARE EXPOSED OVER ALL THE SURFACE OF THE PAINT

FIG. 9

QUANTUM DOTS ARE PARTIALLY OR TOTALLY
FILTERED (COVERED) WITH FADED PAINT PAINT

ENCODING DATA FROM GENETIC TRAITS RELEVANT TO ILLNESS DIAGNOSIS AND HERITAGE

CROSS REFERENCE TO RELATED APPLICATION

This application is a continuation of copending U.S. patent application Ser. No. 15/264,893, filed Sep. 14, 2016, the entire contents and disclosure of which are hereby incorporated herein by reference.

BACKGROUND

This invention, generally, relates to encoding data from genetic traits relevant to illness diagnosis and heritage, and more specifically, to using quantum dots to encode such data.

Genetic information is getting more and more important to treat diseases and emergencies. This information is often not publicly accessible for security reasons related to protecting personal sensitive information and the desire of the owner of the data to keep her or his genetic information private. However, this information may be useful in circumstances where a person is not in condition to provide the data; for example, when she or he is unconscious, or papers or documents having the data are lost or not available at the moment. In addition, people are not used to knowing this useful information, and doctors may be forced to make decisions and to take actions without knowing enough of the patient's relevant medical data.

Also, genetic heritage analysis across a family tree requires genetic data and medical tests that may take hours and resources, with high costs to get results about the influence of traits works. Therefore, this is not accessible for most people around the world, so they are not taking pre-emptive tests based on their probability of incurring a specific illness. As a result, a lot of people are suffering illnesses that could be prevented and treated accordingly. For example, if a woman knows that she has a high probability of developing breast cancer, she may be more likely to take pre-emptive tests to avoid a late diagnosis.

SUMMARY

Embodiments of the invention provide methods and systems for encoding and decoding data from genetic traits. In one embodiment, the invention provides a method comprising encoding genetic traits information, including using quantum dot wavelengths to identify distinct genetic traits, and using numbers of the quantum dots to represent probabilities associated with the traits.

In an embodiment, the invention provides a genetic characteristics decoding system for decoding genetic information encoded using quantum dots. The decoding system comprises a light source for charging the quantum dots, a scanner for scanning the quantum dots to retrieve information from the charged quantum dots, and a processing system for processing the retrieved information to determine quantum dot wavelengths and numbers of the quantum dots. The quantum dot wavelengths are used to identify distinct genetic traits, and the numbers of the quantum dots are used to identify probabilities associated with the genetic traits.

In an embodiment, the invention provides a method of decoding genetic information encoded by analyzing quantum dots. The method comprises charging the quantum dots, scanning the quantum dots to retrieve information from the charged quantum dots, and processing the retrieved information to determine quantum dot wavelengths and numbers of the quantum dots. The quantum dot wavelengths are used to identify distinct genetic traits, and the quantum dot numbers are used to identify probabilities associated with the genetic traits.

In embodiments of the invention, the quantum dot (QD) color represents a trait, and the number, or intensity of the color, represents a probability, as a percentage of a base number, associated with that trait.

Embodiments of the invention encode, decode and combine data of genetic traits like disease predispositions or genetic characteristics compliance. The wavelengths (or colors) of the quantum dots are used to identify the distinct genetic traits, and the numbers of these nano-crystals represent the probabilities of the traits. This way, by mixing the quantum dots in a varnish, personal information can be securely encoded in a color, where the key to decoding the information is the identification of a person plus the color itself.

Embodiments of the invention are relevant to several aspects of health information systems:
a. personal health data: every person has the right for privacy;
b. data availability: in emergency cases, it is necessary to be able to gather as much data as possible about the affected person in a faster and more convenient way; and genetic analysis of heritage: fast processing methods of genetic traits are useful to discover and evaluate characteristics of parents and children.

Embodiments of the invention provide a number of benefits. One important benefit is that personal health related information is securely encoded. The key to decoding the information is the owner itself. Another significant benefit is that a large set of data can be physically stored in minimal space and attached to, for example, profiles and personal ID cards. Also, with this invention, data encoding and decoding can be done systematically.

DETAILED DESCRIPTION

Embodiments of the invention provide a method and system to encode data from genetic traits relevant to illness diagnoses and heritage. Generally, this is done by mixing quantum dots (QDs) into a varnish or other coating in a way that represents the encoded information. For instance, the wavelengths (or colors) of the quantum dots may represent distinct genetic traits or illnesses, and the numbers of these nano-crystals (the intensities of the colors) represent probabilities associated with the genetic traits or illnesses. This way, by mixing the quantum dots in a varnish, personal information about a person can be securely encoded in a color, where the key to decoding the information is a unique value, associated with the person, such as the person's identification or other unique biometric identification plus the color itself.

Quantum dot materials are luminescent inorganic semiconductor nanoparticle materials that emit light when appropriately excited by photo- or electro-excitation. The light emission of quantum dots is due to quantum confinement of electrons and holes. An advantage of quantum dots is that they can be tuned so that they emit any desired wavelength (color) as a function of their size, by using one material only and the same synthetic process. For example, in a nanoparticle size range of from about 2 to about 10 nm, one can obtain a full range of colors from the visible range of the spectrum. In addition, quantum dots posses improved fatigue resistance when compared with organic dyes. Another advantage of quantum dots is their narrow emission bands, which increases the number of possible wavelength choices for designing customized colors.

The quantum dots are mixed in a liquid or suitable fluid carrier, for example, varnish, paint, stain, or other sealant or mixture used for coloring, covering and/or sealing a surface, that is applied to a surface by, for example, brushing spraying or other topical applications used for painting, coating or sealing surfaces. The quantum dots may be mixed in the fluid in any suitable way. The quantum dots may be incorporated into the coating either directly as individual particles, or as incorporated into a carrier matrix, which may be formed by a polymer, inorganic, organic, or metallic substrate.

A variety of types of coatings and a variety of types of quantum dots may be used in embodiments of the invention. For instance, as mentioned above, the coating may be a varnish.

Figure 1:
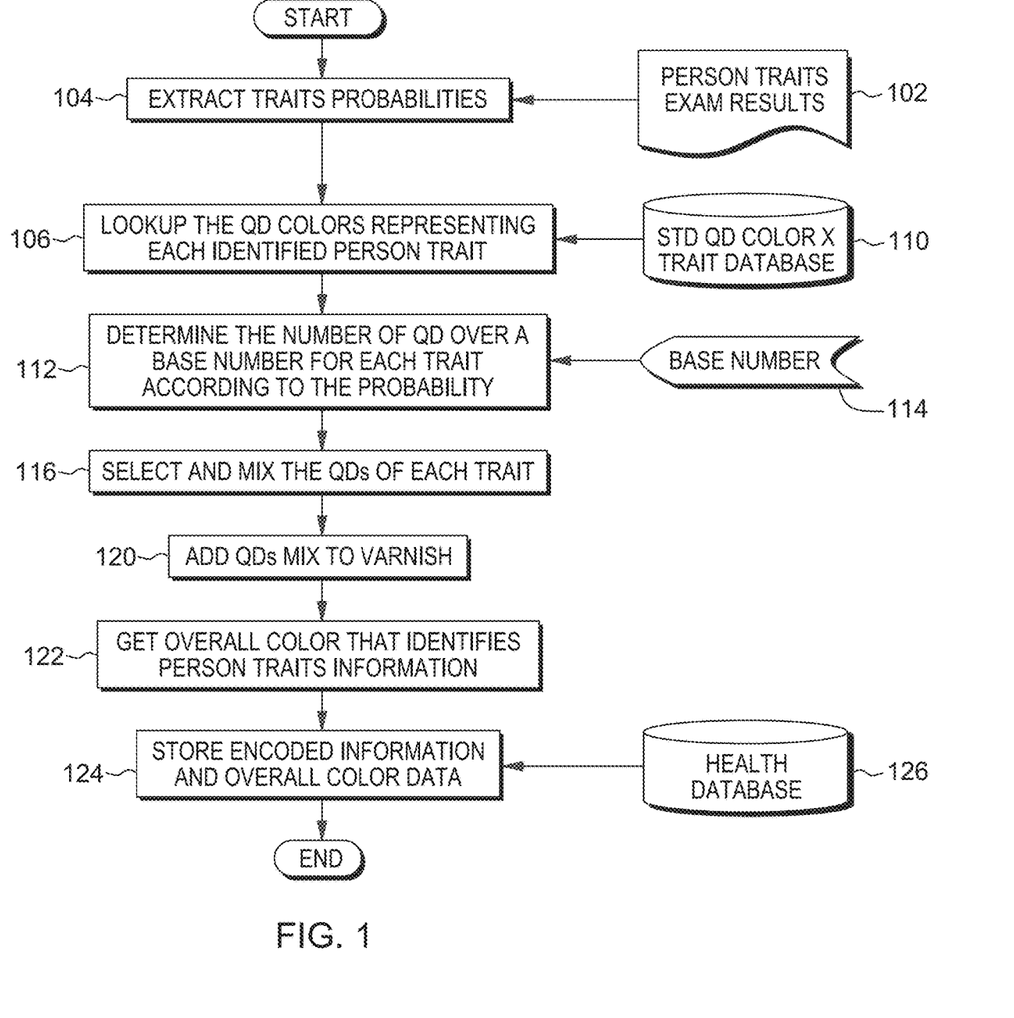
FIG. 1 illustrates a procedure to obtain a paint varnish containing encoded genetic trait information using quantum dots.

FIG. 1 illustrates an example of the invention used to encode personal information. This example method is intended to obtain a paint varnish containing encoded genetic traits information using quantum dot wavelengths (or colors) to identify distinct genetic traits and the numbers of these nano-crystals to represent the probabilities of the traits.

At 102, a person takes exams to get genetic disease predispositions or genetic characteristic compliance. At 104, for every disease and characteristic, a probability value is obtained. For example, the person may have a 20% probability of getting diabetes, a 40% probability of developing lung cancer, and a 70% probability of getting celiac disease. The test results may also show, for example, that there is a 75% probability that the person is blond, a 70% probability that he or she has strong bones, and a 50% probability that the person has a pollen allergy resistance.

At 106, the QD colors representing each identified trait of the person are looked-up from a database 110. For every disease and characteristic, a quantum dot is created. The size of the quantum dot, which defines the color the quantum dot exhibits, identifies the disease or characteristic the quantum dot represents. The size scale for quantum dots is managed separately for diseases and characteristics. For example, diabetes may be represented by 20 nm QDs, lung cancer may be represented by 40 nm QDs, and celiac disease may be represented by 60 nm QDs. The characteristic of being blond may be represented by 10 nm QDs, having strong bones may be represented by 30 nm QDs, and having pollen allergy resistance may be represented by 50 nm QDs.

At 112, a number of QDs over a base number is determined for each trait according to the probability associated with the trait. The base number for these traits is obtained at 114. In an embodiment, a percentage of a base number may be determined.

For example, the base number may be ten million. With the above-listed percentages and quantum dot sizes, diabetes would be represented by two million (20% of ten million) quantum dots of 20 nm, lung cancer would be represented by four million (40% of ten million) quantum dots of 40 nm, and celiac disease would be represented by seven million (70% of ten million) quantum dots of 60 nm. The characteristic of being blond would be represented by 7.5 million (75% of ten million) quantum dots of 10 nm, strong bones is represented by seven million (70% of ten million) quantum dots of 30 nm, and pollen allergy resistance is represented by five million (50% of ten million) quantum dots of 50 nm.

At 116, the QDs of each trait are selected and mixed, and at 120, the QDs are added to a varnish. The result is a varnish of a certain color that is associated with personal identification data of the person. At 122, the overall color that identifies the person's trait information is obtained, and at 124, the encoded information and overall color data are stored in a health database 126.

Figure 2:
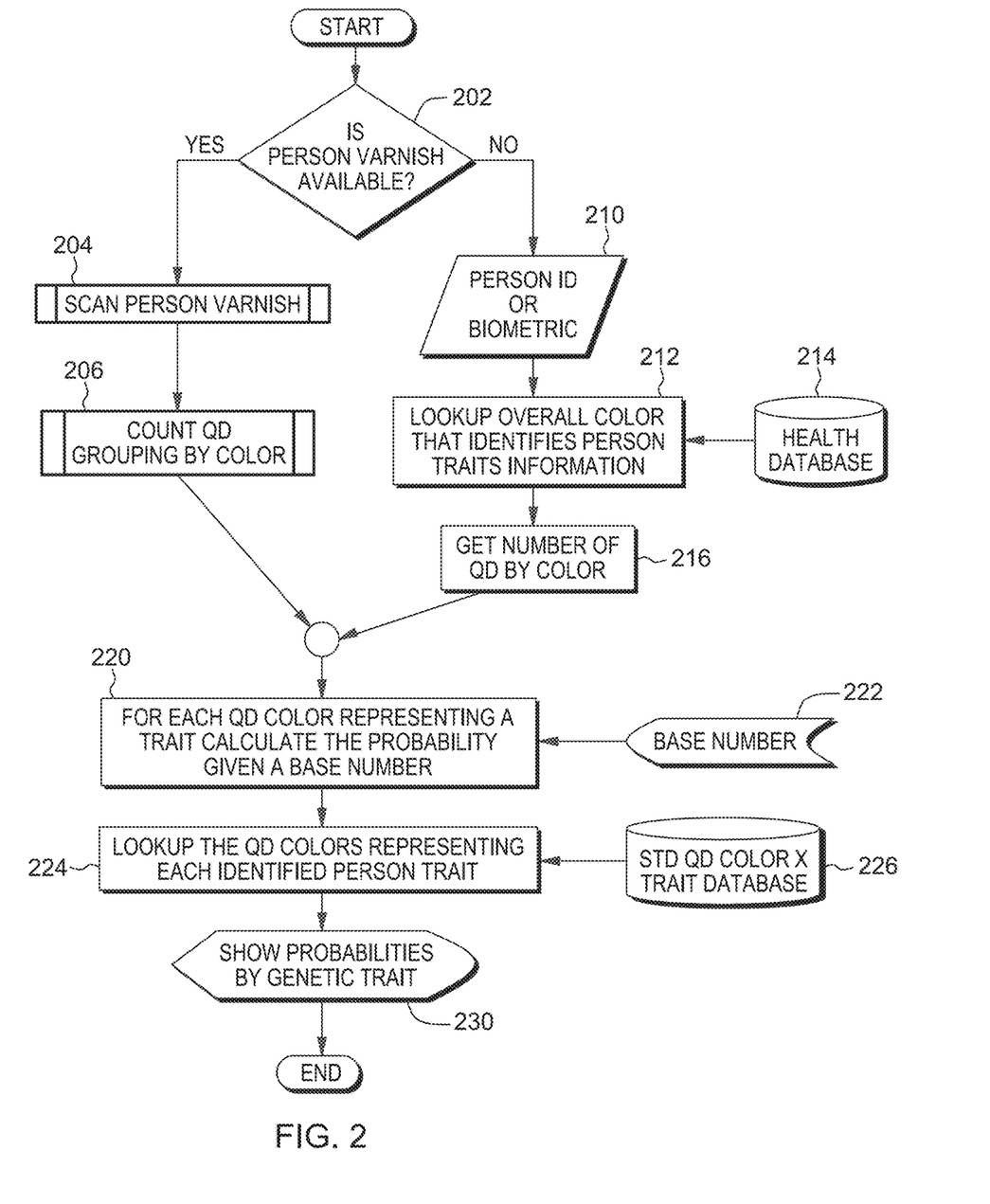
FIG. 2 shows a procedure to decode genetic traits data from a varnish created with the method of FIG. 1.

FIG. 2 shows an example of the invention used to decode genetic traits data for a person from a varnish created with the method of FIG. 1, by interpreting the color and quantum dots readout. Generally, in this method, the person presents his or her identification or biometric, and the color for that ID is retrieved. If the varnish that contains the encoded data is available, the varnish is scanned. Else, if the color is available in a database, the relation of conforming colors is obtained. The percentage of the quantum dots of each color is obtained, and this give the probability value for disease predisposition or genetic characteristic compliance. The colors (sizes) of the conforming quantum dots are obtained and this give the disease and/or characteristics encoded.

More specifically, step 202 in this method is to determine if the varnish that contains a person's encoded data is available. If the varnish is available, the varnish is scanned, at 204, and counts of the QDs are grouped by color, at 206. If, at 202, the varnish is not available, then at 210, the person's ID or biometric information is obtained. At 212, the overall color that identifies the person's traits information is looked-up in a health database 214, and at 216, the number of QDs by color is obtained.

From steps 206 and 216, the two branches of the method merge. At 220, for each QD color representing a trait, a probability is calculated, given a base number that is obtained from 222. At 224, the QD colors representing each identified trait of the person are looked-up in a database 226 that give the standard QD colors by trait; and at 230, the probabilities by genetic trait are shown.

Figure 3A:
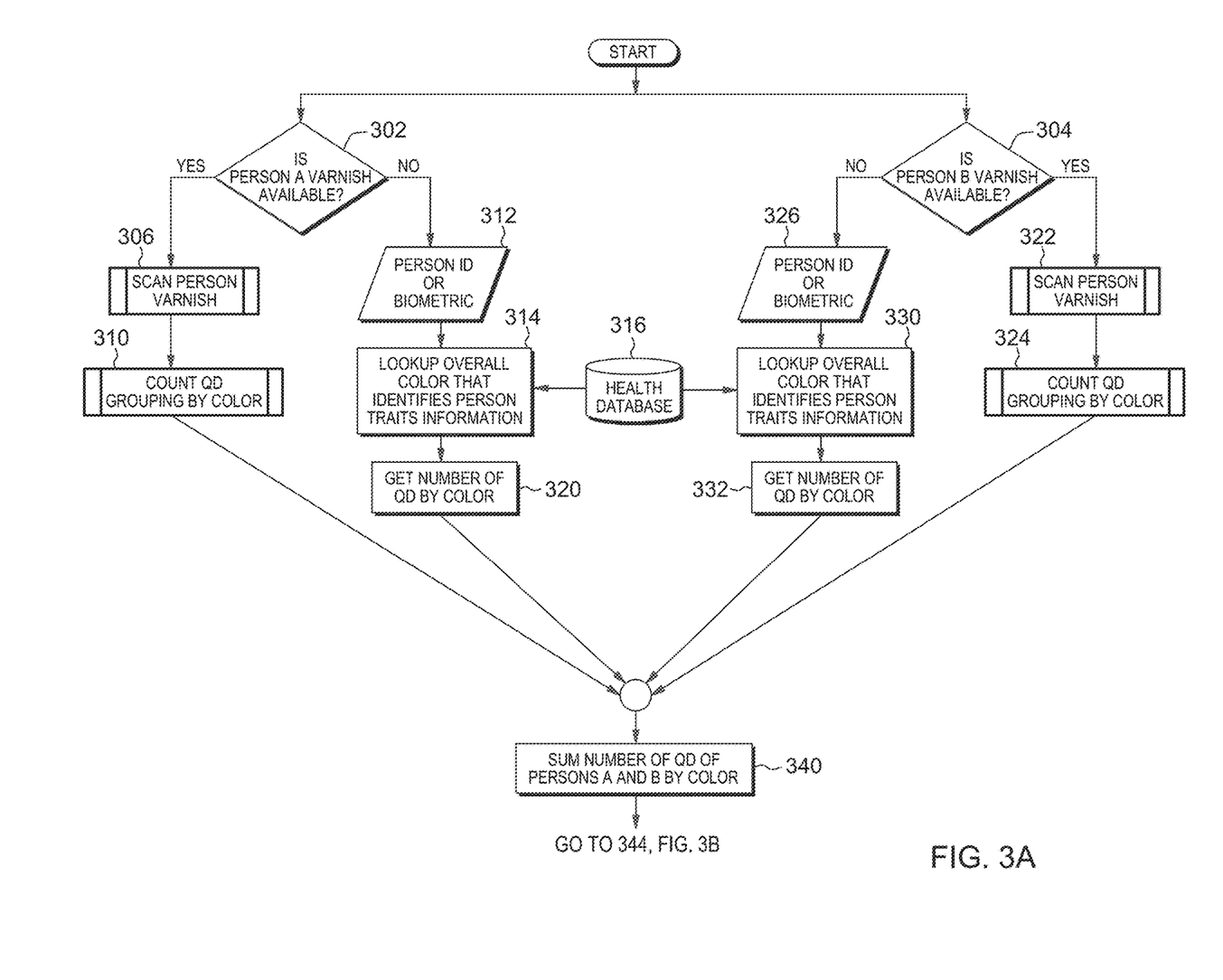
FIGS. 3A and 3B illustrate an analysis of the genetic heritage of two persons in relation to their children based on the combination of encoded genetic information of the parents.
Figure 3B:
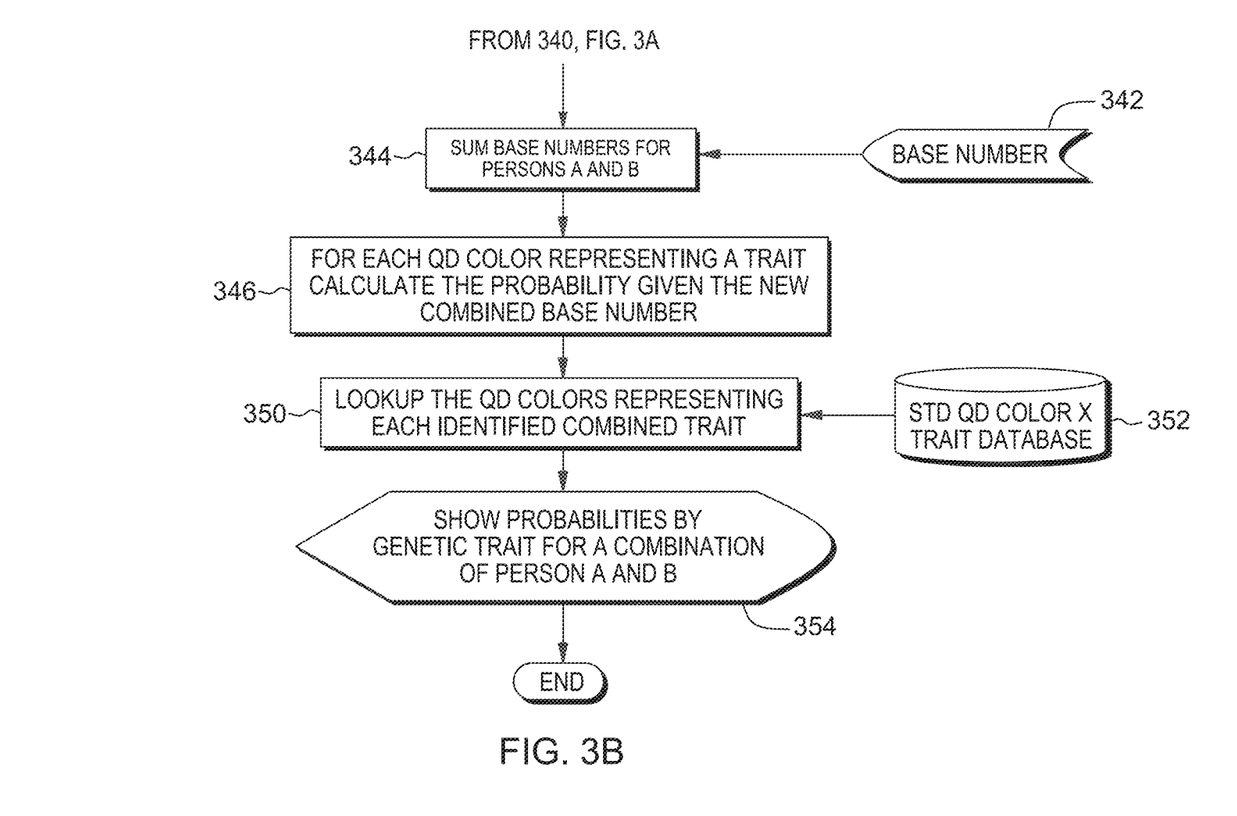

Embodiments of the invention allow a rapid analysis of genetic heritage of two persons towards their children based on the combination of the varnishes of the parents and the interpretation of the quantum dot wavelengths and numbers in the new, combined varnish. FIG. 3 illustrates an example analysis of the genetic heritage of two people in relation to their children based on the combination of encoded genetic information of the parents.

Generally, in this method, the varnish of parent A is combined with the varnish of parent B, taking into account that the base number of quantum dots is summed. The resulting varnish is scanned, and the percentage of quantum dots of each color is obtained. This gives the probability values for disease predispositions or genetic characteristic compliance. The colors (sizes) of the conforming quantum dots are obtained, and this give the diseases and/or characteristics encoded.

In the method of FIGS. 3A and 3B, steps 302 and 304 are to determine if the varnishes for persons A and B, respectively, are available. If the varnish of person A is available, the varnish is scanned, at 306, and counts of the QDs are grouped by color, at 310. If, at 302, the varnish is not available, then at 312, the person's ID or biometric information is obtained. At 314, the overall color that identifies the person's traits information is looked-up in a health database 316, and at 320, the number of QDs by color is obtained.

If the varnish of person B is available at 304, the varnish is scanned, at 322, and counts of the QDs are grouped by color, at 324. If, at 304, the varnish is not available, then at 326, the person's ID or biometric information is obtained. At 330, the overall color that identifies the person's traits information is looked-up in the health database 316, and at 332, the number of QDs by color is obtained.

The branches of the method of FIGS. 3A and 3B merge from steps 310, 320, 324 and 332. At step 340, the numbers of the QDs of persons A and B are summed by color. The base numbers of persons A and B are obtained from 342 and summed at 344. At 346, for each QD color representing a trait, a probability is calculated, given the new, combined base number. At 350, the QD colors representing each identified combined trait are looked-up in a database 352 that give the standard QD colors by trait; and at 354, the probabilities by genetic traits for the combination of persons A and B are shown.

Any suitable scanning or read-out system may be used to analyze a varnish to determine the numbers and the wavelengths of the quantum dots in the varnish. In a method of scanning or reading a varnish, the quantum dots (essentially nanocrystals of certain semiconductors) are excited before the varnish is scanned. This excitation makes the wavelengths of the light emitted from a quantum dot controlled by the size of the nanocrystal particle and the level of confinement of the electrons within the particle. This excitation can be achieved by a scanner by introducing a small electrical charge to the scanned surface.

Figure 4:
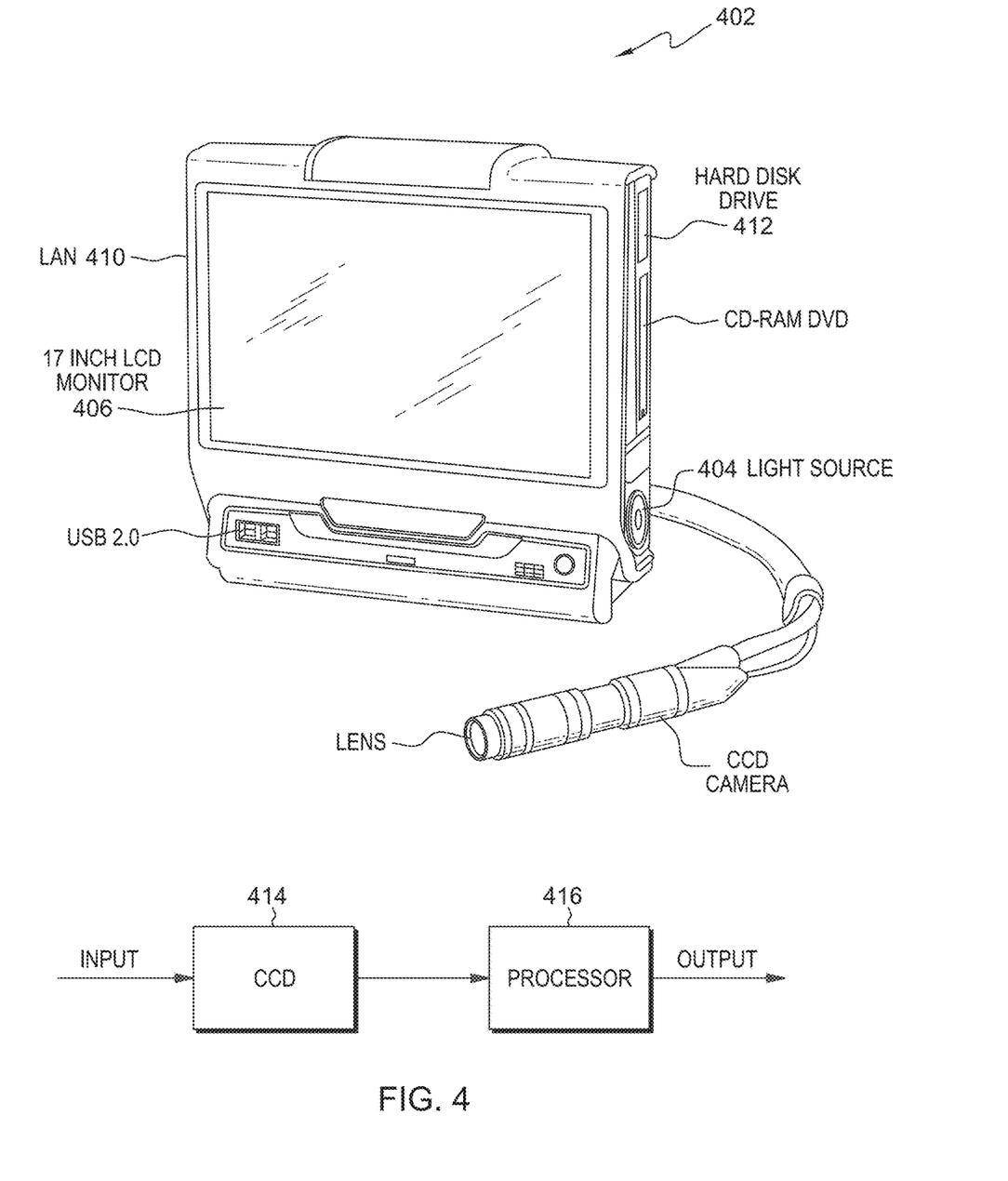
FIG. 4 shows a portable microscope that may be used in embodiments of the invention to scan a varnish for quantum dots.

For example, FIG. 4 illustrates a reader or scanner 402 that may be used in embodiments of the invention. This reader includes light source 404, LCD monitor 406, LAN connection 410, and hard disk drive 412. Also, as schematically illustrated in FIG. 4, the reader includes a CCD camera 414, and a processor 416 for processing the output of the CCD camera. The reader 402 may be a portable microscope that has two types of light—white light and black light. Under the white light, the reader determines the visible color of the sample, also referred to as the "filter color." Then, the black light is used to make the QDs fluoresce, and the system counts the amount of QDs by wavelength (after applying the "unfiltering" by digital means).

In the method of scanning or reading the quantum dots, the detected light emitted from the quantum dots may be affected by a number of factors including chromatic aberration and filtering of the light by the varnish.

Figure 5:
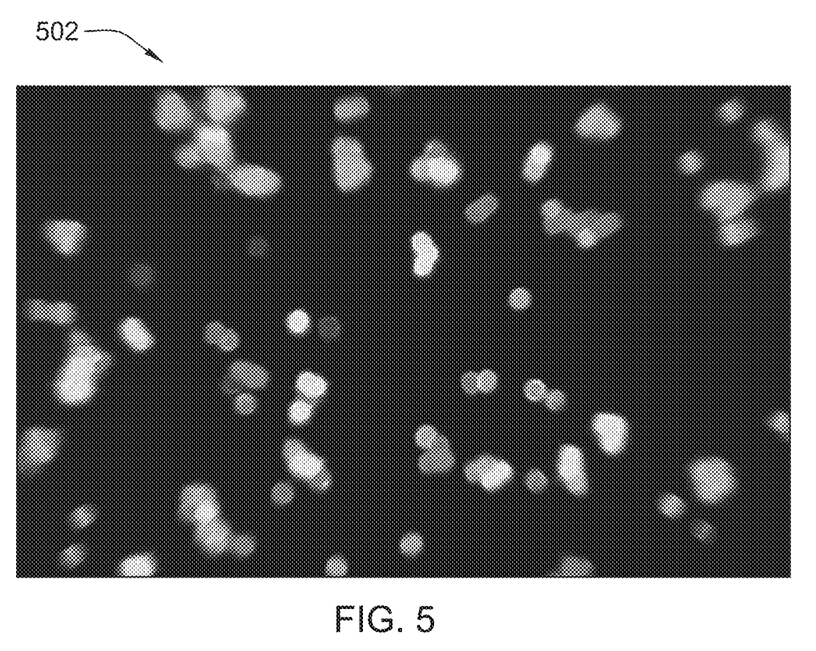
FIG. 5 illustrates an image of a scanning of quantum dots with chromatic aberration.
Figure 6:
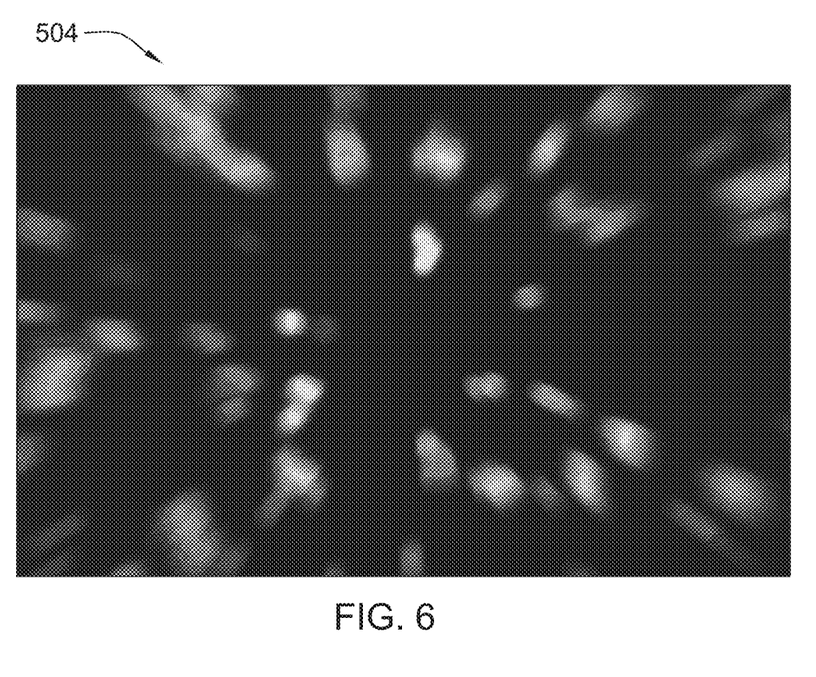
FIG. 6 shows another image of a scanning of quantum dots with chromatic aberration.

FIGS. 5 and 6 show images 502 and 504 of a scanning of quantum dots with chromatic aberration. Chromatic aberration manifests itself as "fringes" of color along boundaries that separate dark and bright parts of the image, because each color in the optical spectrum cannot be focused at a single common point. Since the focal length f of a lens is dependent on the refractive index n, different wavelengths of light will be focused on different positions. Chromatic aberration makes QD counting more difficult, or impossible in the case of the image 504.

With reference to FIG. 5, the total amount of each color may be correct, but not in the right location, making the picture color very distorted. This may make the "count" of QDs per square inch to be difficult if not impossible, based on the wide variety of frequencies in the optical spectrum. A way to address this is to use the magnitude of the light rather than the count itself, but this requires filtering out any unwanted light waves so the magnitude (amount of Lux) on the specific wavelength is correctly measured.

Figure 7:
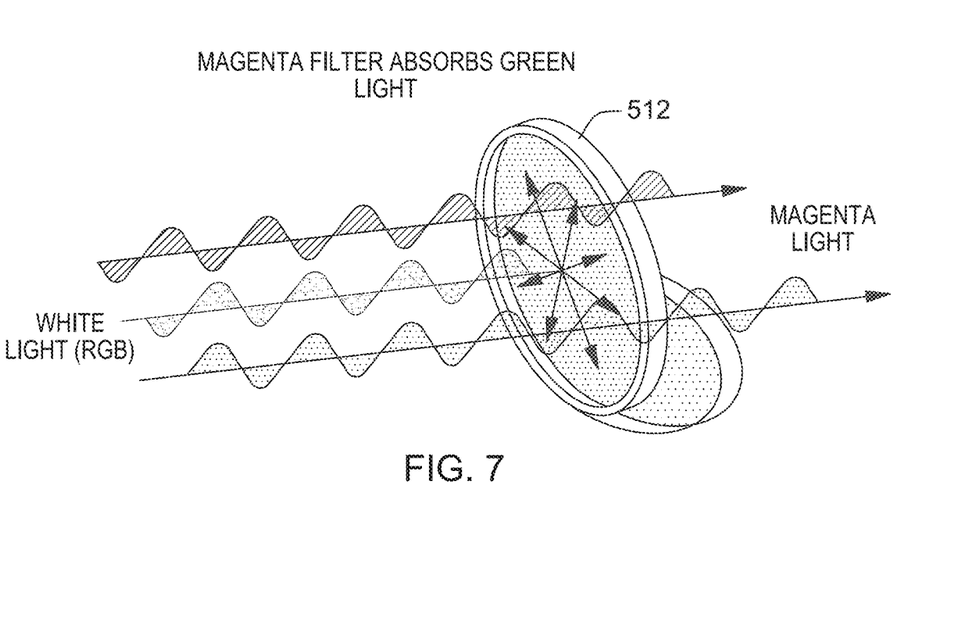
FIG. 7 illustrates an example of how a varnish can work as a filter, affecting the wavelength of light emitted by quantum dots in the varnish.
Figure 8:
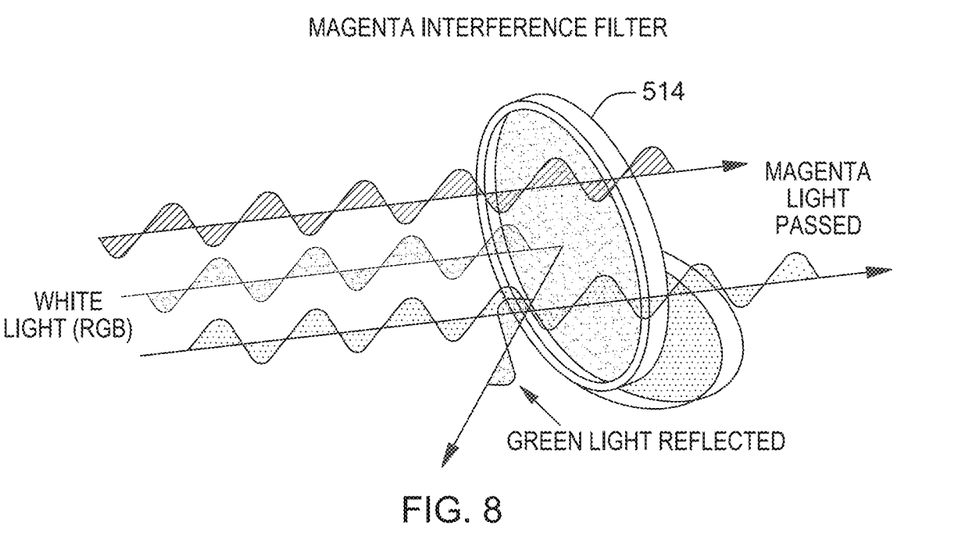
FIG. 8 shows another example of how a varnish can affect the wavelength of light emitted by quantum dots in the varnish.

Additionally, in embodiments of the invention, a filtering effect is generated by the color of the varnish itself. FIGS. 7 and 8 are examples of how a varnish could work as a filter, affecting the light wavelength (color) emitted by the quantum dots that are partially or totally covered by the varnish. As illustrated in FIG. 7, white light (RGB) is directed onto filter 512. The filter absorbs green light, and the magenta light passes through the filter. As shown in FIG. 8, the filter 514 reflects the green light, and magenta light passes through the filter.

The filtering effect of the varnish needs to be counteracted in order to properly read the data. Since the optical filters are completely described by their frequency response, and the media works as an absorptive filter, the current color of the varnish and how the varnish color affects the wavelengths of interest can be calculated. By using a digital filtering technique, the data can be read without needing to directly count all of the QDs per square inch, and rather by identifying the magnitude of the response to a UV light input or an electrical charge to the area being scanned.

Note that each of the two above-mentioned techniques for stimulating the UV light will use a different magnitude base to determine the amount of QDs per square inch per light frequency, as the electrical stimulation will generate some "bleed through" of QDs in lower levels of the varnish coating, whereas the UV readout will not have that level of penetration into the media.

Digital Filters are used so only the correct wavelengths are read, comprised of the addition of all of the wavelengths generated by the QDs of the same type under the influence of the UV or electrical stimulation. This means that the method needs to correct any unwanted wavelengths generated by the QD light shining through the coats of varnish that act as filters, and as mentioned above, this is needed so a correct value can be read.

Figure 9:
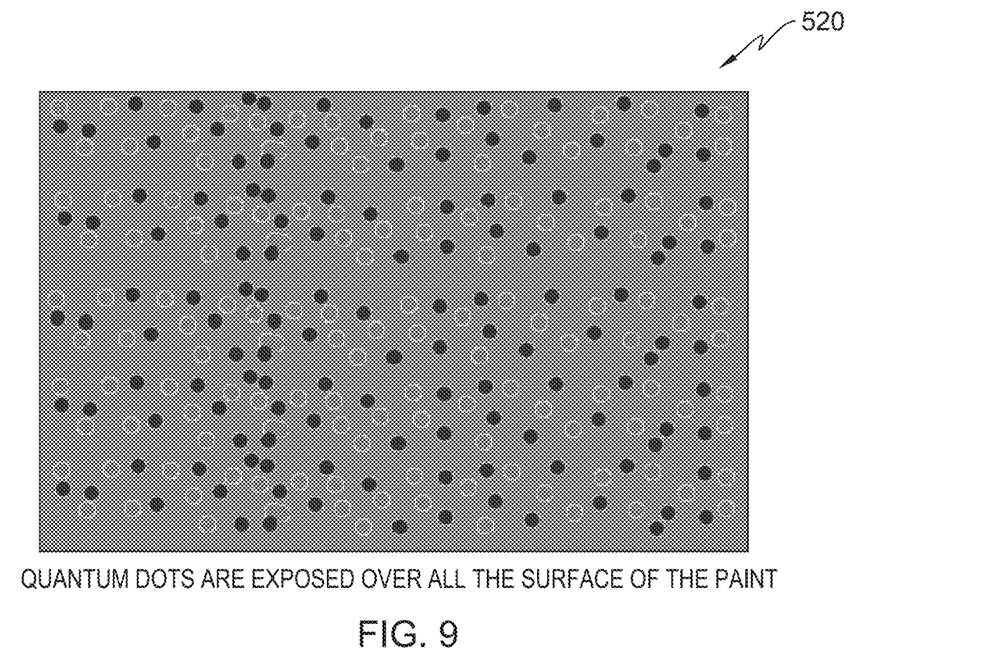
FIG. 9 shows a varnish sample in which quantum dots are exposed over the surface of the varnish.

The filtering effect is especially important for extracting the original color from coated surfaces. An optimal scenario of a varnish is one where the QDs are all exposed over the surface of the varnish, subsequently it is easier to process the scan. FIG. 9 represents this scenario at 520.

Figure 10:
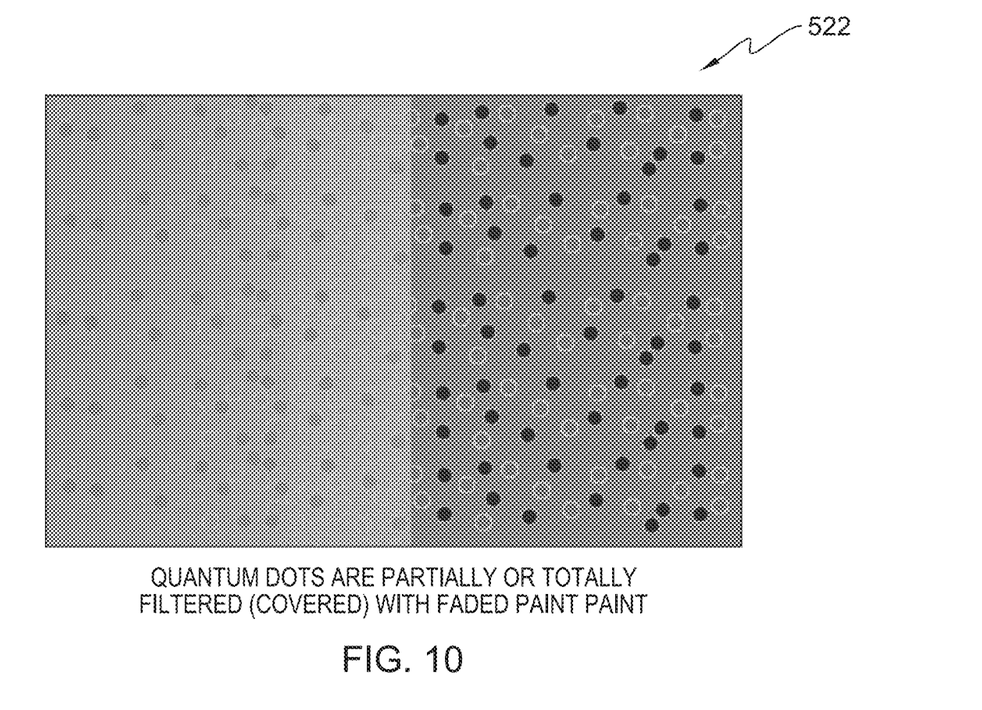
FIG. 10 shows a varnish sample in which quantum dots are partially or totally filtered (covered) with varnish.

But the real scenario, like in FIG. 10 at 522, is one where the QDs are partially or totally filtered (covered) with varnish, which may imply its real wavelength is also hampered partially. Therefore the digital techniques mentioned above are applied in order to correctly interpret the samples.

FIGS. 11-14 illustrate principles of the filtering technique in more detail.

Figure 11:
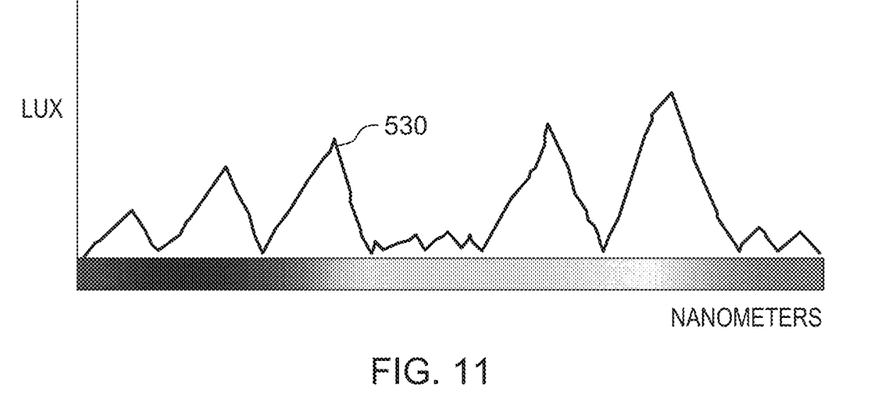
FIG. 11 shows the results of an initial varnish scan in an embodiment of the invention.
Figure 12:
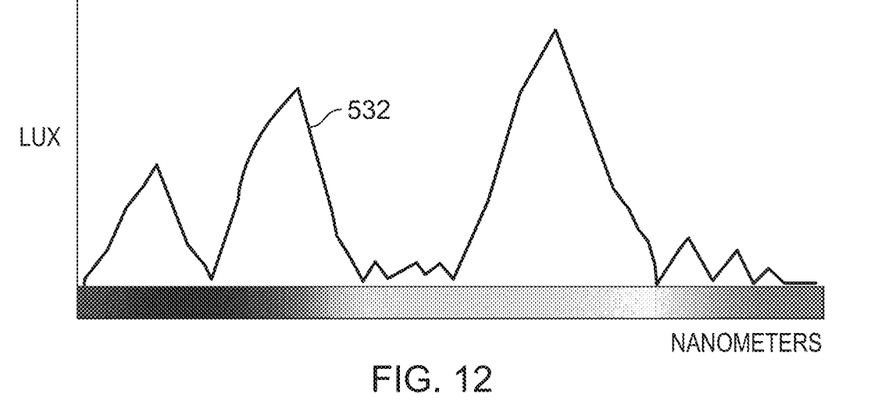
FIG. 12 illustrates the count of quantum dots in distinct colors in an embodiment of the invention.

FIG. 11 shows at 530 the results of an initial scan. This scan is performed to get the set of current colors that may be obstructing (filtering) the real QDs color in deeper layers. As shown in FIG. 12 at 532, a count is obtained of QDs in distinct colors after charging them. Some QDs wavelength will be filtered by the varnish, so this measure has to be corrected.

The next step is reverse filtering applying the initial scan over the QD scan. The filter is obtained by determining how inversely the varnish affects QD color.

Figure 13:
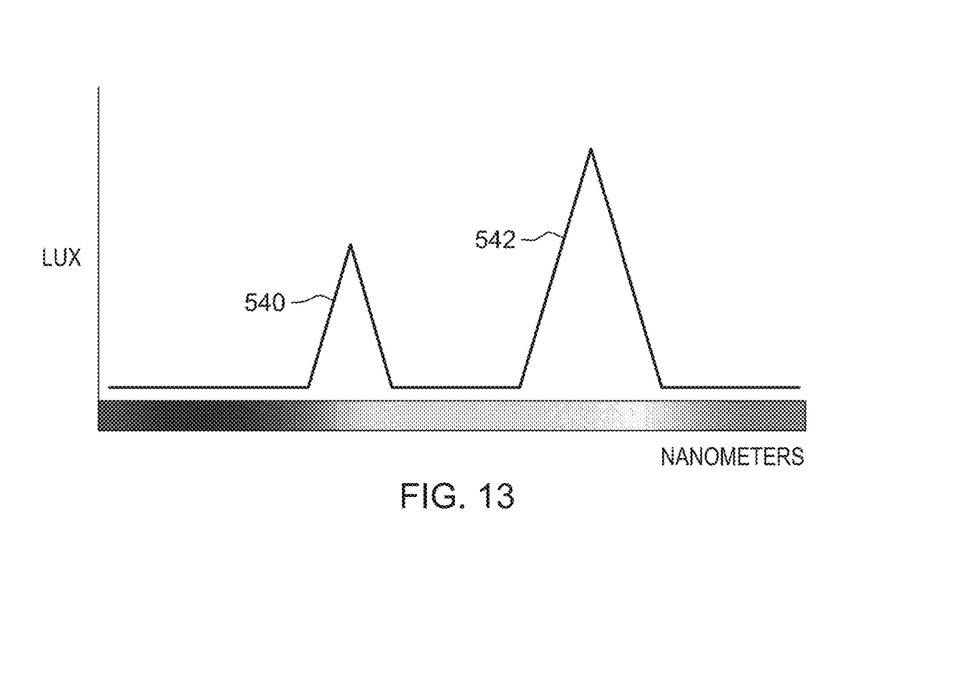
FIG. 13 shows a filter example based on the scanned images of FIGS. 11 and 12.
Figure 14:
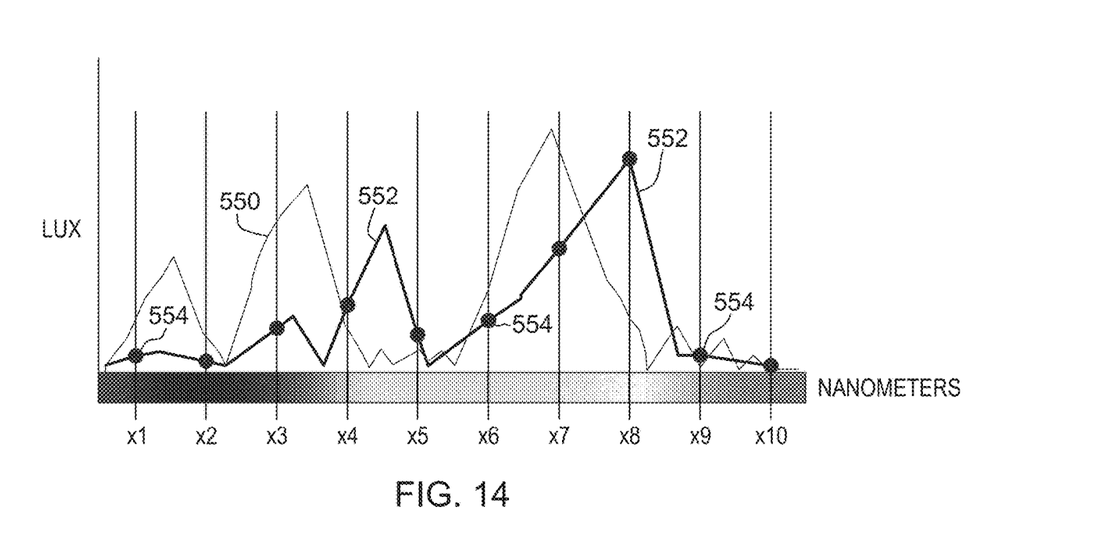
FIG. 14 shows a new filter applied over the quantum dot readout of FIG. 12.

FIG. 13 is a filter example based on the previous scan images. There are mainly two wavelength ranges (the peaks) 540 and 542 affected by the varnish filtering. As shown in FIG. 14, the new filter is applied over the QD scan (gray line) 550. The black line 552 is the corrected QD count. This is an example of QD correction based on the previous examples of QD count by color and filter.

The lines x1 to x10 represents the colors (or wavelengths) of QDs known to exist in the varnish. Following the example, the points 554 at the x1 to x10 lines represent the number of QDs for each color in a squared inch: x1=2, x2=0, x3=8, x4=14, x5=5, x6=10, x7=20, x8=30, x9=1, x10=0.

The total sum is 90 QDs. If a concentration of 100 QDs per square Inch is assumed, 10 QDs are missing; however, the "color" is derived from the percentages of the QDs found in the sample. The tone (how light or dark) is derived from the difference between the expected 100 QD per square inch and the 82 color definition QDs registered. This calculation is based on 82. Since there may be additional QDs in the varnish that relate to metadata (year and manufacturer of the varnish, as an example), not all of the QDs may be relevant to the color of the varnish. So in this example, it is stipulated that x1, x5, x9 are the respective markers for a paint or tint manufacturer, base type and year of manufacture.

This will yield the exact color, as the tint and base manufacture processes and formulas may vary between the years and manufacturers. This will give the most accurate measurement of the original color of the varnish that had been applied. Also, the expected amount of QDs is based on these "key" QDs found, as this is the only known amount (For example, all manufacturers must place 854000 QDs of their ID per gallon of paint . . . ) which will give a known reading to make the necessary mathematical calculations as shown.

Therefore:
x1->Manufacturer ID=2
x5->Base type ID=5
x9->Year of manufacture ID=1

Now, with the rest of 82 x's QDs, the correct combination is found using cross multiplication to find the exact percentage of each color of QD in the varnish:

x3->8×100/82=9.76%
x4->14×100/82=17.07%
x6->10×100/82=12.20%
x7->20×100/82=24.39%
x8->30×100/82=36.59%

This is the concentration of each color of QD in a varnish after filtering, for a given manufacturer, base and year.

Figure 15:
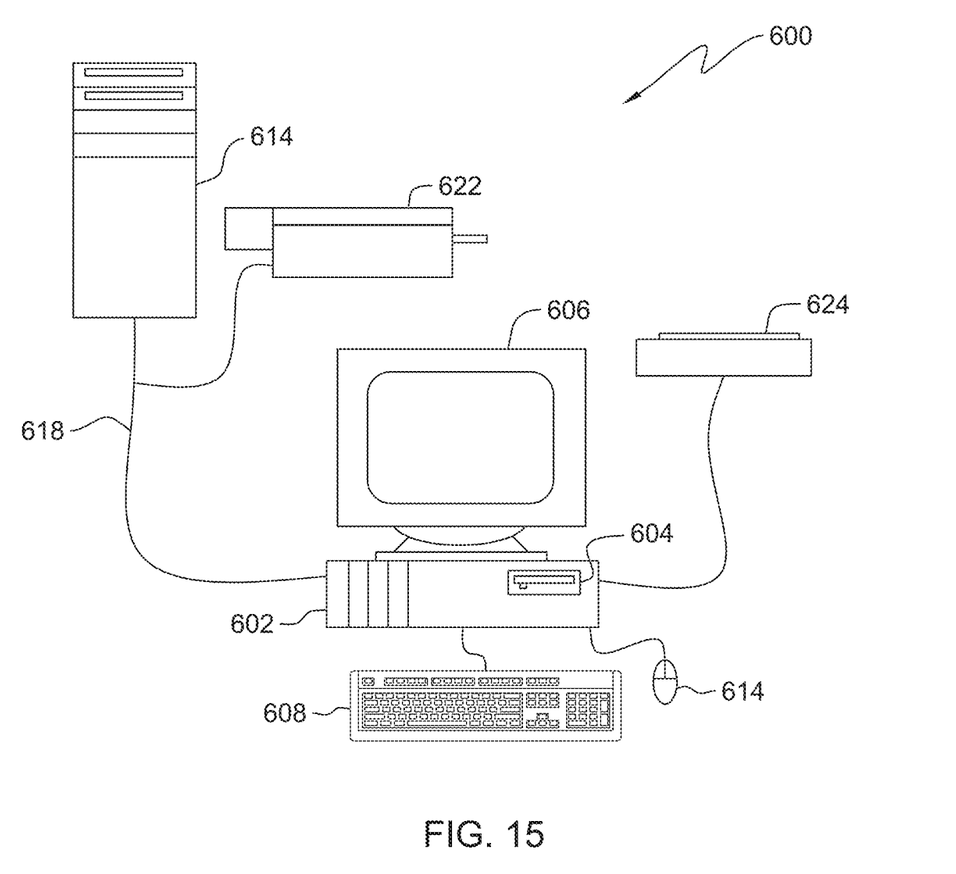
FIG. 15 shows a computing environment that may be used in embodiments of this invention.

A computer-based system 600 in which aspects of the invention may be carried out is depicted in FIG. 15. The computer-based system 600 includes a processing unit 602, which houses a processor, memory and other systems components (not shown expressly in the drawing) that implement a general purpose processing system, or computer that may execute a computer program product. The computer program product may comprise media, for example a compact storage medium such as a compact disc, which may be read by the processing unit 602 through a disc drive 604, or by any means known to the skilled artisan for providing the computer program product to the general purpose processing system for execution thereby.

The computer program product may comprise all the respective features enabling the implementation of the inventive method described herein, and which—when loaded in a computer system—is able to carry out the method. Computer program, software program, program, or software, in the present context means any expression, in any language, code or notation, of a set of instructions intended to cause a system having an information processing capability to perform a particular function either directly or after either or both of the following: (a) conversion to another language, code or notation; and/or (b) reproduction in a different material form.

The computer program product may be stored on hard disk drives within processing unit 602, as mentioned, or may be located on a remote system such as a server 614, coupled to processing unit 602, via a network interface 618 such as an Ethernet interface. Monitor 606, mouse 614 and keyboard 608 are coupled to the processing unit 602, to provide user interaction. Scanner 624 and printer 622 are provided for document input and output. Printer 622 is shown coupled to the processing unit 602 via a network connection, but may be coupled directly to the processing unit. Scanner 624 is shown coupled to the processing unit 602 directly, but it should be understood that peripherals might be network coupled, or direct coupled without affecting the performance of the processing unit 602.

While it is apparent that the invention herein disclosed is well calculated to achieve the features discussed above, it will be appreciated that numerous modifications and embodiments may be devised by those skilled in the art, and it is intended that the appended claims cover all such modifications and embodiments as fall within the true spirit and scope of the present invention.

The invention claimed is:

1. A method of using quantum dots for encoding in a carrier genetic related disease data, the method comprising:
    selecting one or more quantities of quantum dots for encoding disease information, each of said quantities of quantum dots comprising a selected number of quantum dots having a specified size and emitting light at a specified wavelength, including:
    mixing the one or more quantities of quantum dots in a carrier;
    using a processing system implementing a scanner for detecting the wavelengths at which the one or more quantities of the quantum dots in the carrier emit light to identify distinct diseases, including representing each of the diseases with a respective one of the sizes of the quantum dots, and using the processing system implementing a scanner for detecting the selected numbers of the quantum dots in the one or more quantities of the quantum dots in the carrier to represent probabilities associated with the diseases, wherein the encoding genetic information further includes identifying one or more diseases associated with a person; and the using the wavelengths of the quantum dots to identify distinct diseases includes identifying a quantum dot size to represent each of the one or more diseases; and wherein the detecting the selected numbers of the quantum dots to represent probabilities associated with the diseases includes:

for each of the one or more diseases associated with the person, determining a number of quantum dots of the identified quantum dot size that represent said each of the diseases, to represent one of the probabilities, said one of the probabilities being associated with the each disease; and wherein the encoding disease information further includes using the determined numbers of the quantum dots of the identified quantum dot sizes to create a color representation of the one or more diseases associated with the person.

2. The method according to claim 1, wherein the identifying a quantum dot size to represent each of the one or more diseases includes performing a look-up of quantum dot sizes representing the one or more diseases in a database storing quantum dot sizes for the one or more diseases.

3. The method according to claim 1, wherein the identifying a quantum dot size to represent each of the one or more diseases includes identifying a respective one quantum dot size for each of the one or more diseases.

4. The method according to claim 1, wherein the encoding disease information further includes storing the color representation in a health database.

5. The method according to claim 1, wherein the mixing the quantum dots in a carrier includes mixing the determined numbers of quantum dots of the identified quantum dot sizes into the carrier to encode the one or more diseases associated with the person in the carrier.

6. The method according to claim 1, wherein the determining a number of quantum dots of the identified quantum dot size that represents said each of the diseases, to represent one of the probabilities includes determining each of said numbers as a respective one percentage of a defined base number.

7. The method according to claim 6, wherein the determining each of said numbers as a respective one percentage of a defined base number includes obtaining the defined base number from a database.

8. A genetic characteristics decoding system for decoding genetic related disease information encoded using one or more quantities of quantum dots in a carrier, each of said quantities of quantum dots comprising a selected number of quantum dots having a specified size and emitting light at a specified wavelength, the decoding system comprising:

a light source for charging the one or more quantities of quantum dots in the carrier;

a scanner for scanning the carrier to retrieve information from the charged one or more quantities of quantum dots; and a processing system for processing the retrieved information from the one or more quantities of quantum dots in the carrier to determine the wavelengths of the one or more quantities of quantum dots in the carrier to identify distinct diseases, and to determine the numbers of the quantum dots in the one or more quantities of the quantum dots in the carrier to identify probabilities associated with the diseases, wherein each of the diseases is represented by a respective one quantum dot size, the processing system further processing the retrieved information to determine a plurality of distinct quantum dot wavelengths, each of the distinct quantum dot wavelengths identifying one of the distinct diseases; and the processing system identifying, for each of the diseases, a number of quantum dots of one of the distinct quantum dot wavelengths representing one of the probabilities, said one of the probabilities being associated with the each disease.

9. The decoding system according to claim 8, wherein the processing system performs a look-up of quantum dot wavelengths representing the distinct diseases.

10. The decoding system according to claim 8, wherein the processing system converts the numbers of quantum dots to percentages of a defined base number.

11. A method of decoding genetic related disease information encoded by analyzing one or more quantities of quantum dots in a carrier, each of said quantities of quantum dots comprising a selected number of quantum dots having a specified size and emitting light at a specified wavelength, the method comprising:

charging the one or more quantities of quantum dots in the carrier;

scanning the carrier to retrieve information from the charged one or more quantities of quantum dots; and processing the retrieved information from the one or more quantities of quantum dots in the carrier to determine the wavelengths of the one or more quantities of quantum dots in the carrier to identify distinct diseases, and to determine the numbers of the quantum dots in the one or more quantities of the quantum dots in the carrier to identify probabilities associated with the diseases, wherein each of the diseases is represented by a respective one quantum dot size, and the processing the retrieved information includes determining a plurality of distinct quantum dot wavelengths, each of the distinct quantum dot wavelengths identifying one of the distinct diseases; and wherein the processing the retrieved information further includes identifying, for each of the diseases, a number of quantum dots of one of the distinct quantum dot wavelengths representing one of the probabilities, said one of the probabilities being associated with the each disease.

12. The method according to claim 11, wherein the processing the retrieved information further includes performing a look-up of quantum dot wavelengths representing the distinct diseases.

13. The method according to claim 11, wherein the processing the retrieved information further includes converting the numbers of quantum dots to percentages of a defined base number.

* * * * *